(12) United States Patent
Feng (10) Patent No.: US 9,201,230 B2
(45) Date of Patent: Dec. 1, 2015

(54) SYSTEMS FOR AND METHODS OF FACILITATING FOCUSING AN OPTICAL SCANNER

(71) Applicant: ILLUMINA, INC., San Diego, CA (US)

(72) Inventor: Wenyi Feng, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 14/491,708

(22) Filed: Sep. 19, 2014

(65) Prior Publication Data

US 2015/0009491 A1   Jan. 8, 2015

Related U.S. Application Data

(60) Continuation of application No. 12/822,325, filed on Jun. 24, 2010, now Pat. No. 8,867,029, which is a division of application No. 11/084,719, filed on Mar. 18, 2005, now Pat. No. 7,768,638.

(51) Int. Cl.
| | | |
|---|---|---|
| *G01B 9/00* | (2006.01) | |
| *G02B 21/00* | (2006.01) | |
| *G01N 15/14* | (2006.01) | |

(52) U.S. Cl.
CPC ............ *G02B 21/006* (2013.01); *G02B 21/008* (2013.01); *G01N 2015/1452* (2013.01)

(58) Field of Classification Search
CPC ....................................................... G01B 9/00
USPC .......................................................... 356/124
See application file for complete search history.

(56) References Cited

U.S. PATENT DOCUMENTS

| | | | |
|---|---|---|---|
| 5,260,578 | A | 11/1993 | Bliton et al. |
| 5,313,264 | A | 5/1994 | Ivarsson et al. |
| 5,424,552 | A | 6/1995 | Tsuji et al. |
| 5,532,873 | A | 7/1996 | Dixon |
| 5,570,691 | A | 11/1996 | Wright et al. |
| 5,672,880 | A | 9/1997 | Kain |
| 5,754,291 | A | 5/1998 | Kain |
| 5,847,400 | A | 12/1998 | Kain et al. |
| 5,981,956 | A | 11/1999 | Stern |
| 6,016,357 | A | 1/2000 | Neary et al. |
| 6,025,601 | A | 2/2000 | Trulson et al. |
| 6,101,263 | A | 8/2000 | Shimizu et al. |
| 6,181,425 | B1 | 1/2001 | Svetkoff et al. |
| 6,309,601 | B1 | 10/2001 | Juncosa et al. |
| 6,324,479 | B1 | 11/2001 | Friend et al. |
| 6,545,264 | B1 | 4/2003 | Stern |
| 6,545,789 | B1 | 4/2003 | Lemasters |
| 6,548,796 | B1 | 4/2003 | Silvermintz et al. |
| 6,548,810 | B2 | 4/2003 | Zaluzec |

(Continued)

OTHER PUBLICATIONS

Booth et al. "Adaptive aberration correction in a confocal microscope," Apr. 30, 2002, PNAS, vol. 99, No. 9, p. 5788, 5792.

*Primary Examiner* — Roy M Punnoose
(74) *Attorney, Agent, or Firm* — Fletcher Yoder P.C.

(57) ABSTRACT

Systems and methods for facilitating focusing of an image scanner, such as a confocal microscope, are disclosed. Measurement of optical characteristics in certain areas of a test sample are compared to stored or baseline optical characteristic profiles to determine an appropriate correction to properly focus the scanner. In one aspect, the method includes obtaining a dynamic profile at a current detection region of a test sample and associating the dynamic profile to a profile selected from a set of stored baseline profiles. Each of the stored baseline profiles is associated with a correction.

20 Claims, 6 Drawing Sheets

(56) References Cited

U.S. PATENT DOCUMENTS

| | | |
|---|---|---|
| 6,586,750 B2 | 7/2003 | Montagu et al. |
| 6,687,052 B1 | 2/2004 | Wilson et al. |
| 6,757,060 B2 | 6/2004 | Davis et al. |
| 6,791,698 B2 | 9/2004 | Doemens et al. |
| 6,810,140 B2 | 10/2004 | Yang et al. |
| 8,867,029 B2 * | 10/2014 | Feng .................... G02B 21/006 356/124 |
| 2002/0117632 A1 | 8/2002 | Hakamata et al. |
| 2002/0131032 A1 | 9/2002 | Tsuji et al. |
| 2003/0151742 A1 | 8/2003 | Silvermintz et al. |

\* cited by examiner

SYSTEMS FOR AND METHODS OF FACILITATING FOCUSING AN OPTICAL SCANNER

CROSS REFERENCE TO RELATED APPLICATIONS

This application is a continuation of U.S. patent application Ser. No. 12/822,325, entitled "Systems for and Methods of Facilitating Focusing an Optical Scanner," filed Jun. 24, 2010, which is a divisional of U.S. patent application Ser. No. 11/084,719, entitled "Systems for and Methods of Facilitating Focusing an Optical Scanner," filed Mar. 18, 2005, and issued as U.S. Pat. No. 7,768,638 on Aug. 3, 2010, both of which are herein incorporated by reference.

BACKGROUND

The present invention relates generally to the field of imaging. In particular, the invention relates to systems and methods for facilitating the focusing of an imaging device, such as a confocal microscope.

Confocal imaging provides a valuable mechanism for obtaining improved images by filtering out-of-focus interference. Confocal imaging is particularly useful in many biological applications, such as for the identification of biological elements including antigens.

A typical confocal imaging system illuminates a single point or region of a sample such that the illumination irradiance decreases rapidly above and below a focal plane. The single point or region can then be scanned across the entire sample to obtain a complete image.

When confocal imaging is used for surface detection, the focal plane should be accurately determined to obtain the desired image. In such confocal imaging systems, the system is calibrated for a focal plane prior to use of the systems in the field. However, with longer sample slides, for example, a single calibration may be insufficient to account for variations along the length of the slide due to bending or warping, for example. Thus, the imaging system may be calibrated for a scan at one end of the slide, but may be miscalibrated for a scan at the opposite end or the middle of the slide.

BRIEF DESCRIPTION

Embodiments of the invention facilitate focusing of an imaging system, such as a confocal microscope. Measurement of optical characteristics or other detectable parameters in certain areas of a test sample can be compared to stored or baseline profiles, that relate such parameters to sample coordinates, in order to determine an appropriate correction to achieve a desired focus for the system.

In one aspect, the invention includes a method of facilitating focusing of an imaging scanner. The method includes obtaining a dynamic profile for at least a portion of a current detection region of a test sample and associating the dynamic profile to a profile selected from a set of stored reference profiles. Each of the stored reference profiles is associated with a correction.

In one embodiment, a dynamic profile and a stored reference profile may include values for at least one parameter at two or more points in the sample. In a particular embodiment, the at least one parameter includes at least one of radiation intensity, resolution, contrast, phase and aberration.

In another embodiment, a dynamic profile and a stored baseline profiles include values for at least two parameters at one or more points in the sample. In a particular embodiment, the at least two parameters include at least two of intensity, resolution, contrast, phase and aberration.

In one embodiment, a step of associating a dynamic profile to a reference profile selected from a set of reference profiles includes performing a pattern-matching analysis to select one of the stored baseline profiles having desired level of similarity with the dynamic profile.

A method of the invention may also include applying a correction associated with a selected reference profile such that a detection system (including sample, optical elements, sample stage, etc.) is adjusted for focused detection of the current detection region of a test sample. This step or others included in a method of the invention can be repeated for additional detection regions of the test sample, as desired. In a particular embodiment, the correction specifies adjustment of z-axis translation to change the optical path length between an objective lens and a sample stage accommodating the test sample. A step of applying the correction can include driving at least one of the objective lens, other optical elements, and sample stage along a z-axis direction such that focus is changed.

In one embodiment, a step of obtaining a dynamic profile, reference profile or an optical characteristic of a sample can include using a photodetector. The photodetector may include at least one of a photomultiplier, a charge coupled device (CCD), a complementary metal oxide semiconductor (CMOS), a photomultiplier tube (PMT), an avalanche photodiode detector or a photodiode. A photodetector may be a single element detector or may include a detector array.

In another aspect, a method of focusing an imaging system can include obtaining reference profiles for at least a portion of a calibration region of the imaging system, determining a correction associated with each of the reference profiles, measuring a dynamic profile for at least a portion of a current detection region of the test sample, and associating the dynamic profile of the current detection region to a profile selected from the reference profiles.

Another aspect of the invention includes an imaging system. The system can include a radiation source for illuminating at least a portion of a test sample positioned on a sample stage, a confocal detector adapted to detect radiation emanating from the lightest sample, the confocal scanning arrangement including an objective lens for focusing the radiation at a focal plane, a detector for detection of an intensity of radiation emanating from the sample, and a z-axis focusing arrangement. The z-axis focusing arrangement can include a memory device for storing two or more reference profiles, each of the reference profiles having a corresponding correction, and a processor adapted to determine a correction required for a current detection region by associating a dynamic profile for at least a portion of the current detection region with one of the reference profiles.

In another aspect of the invention, a method of facilitating focusing of an imaging system can include providing a library of reference profiles, wherein each reference profile includes a z-axis variation for at least two points in a detection region, obtaining a dynamic profile including variation in an optical property for at least two points of a detection region of the test sample, comparing the dynamic profile to reference profiles in the library, identifying a best fit reference profile for the dynamic profile from the library of reference profiles, and making an adjustment to the imaging system based on the best fit reference profile.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Detection systems useful for imaging planar surfaces, for example, those having confocal scanning detectors, can be highly sensitive to variations in focus plane. Variations that can affect focus include, but are not limited to, optical aberrations such as field curvature, astigmatism or coma; or inconsistency in a surface being imaged such as tilt relative to the optical axis or variable surface texture resulting in changes in relative elevation from one point to another. The present invention provides a method of focusing a detection system based on a profile of a detectable characteristic of a sample, such as field intensity for light emanating from the sample vs. physical coordinates of the sample. Accordingly, in systems where variations occur in the optics, sample or both, the method can be used to determine a desired focus for imaging the surface of the sample.

Figure 6:
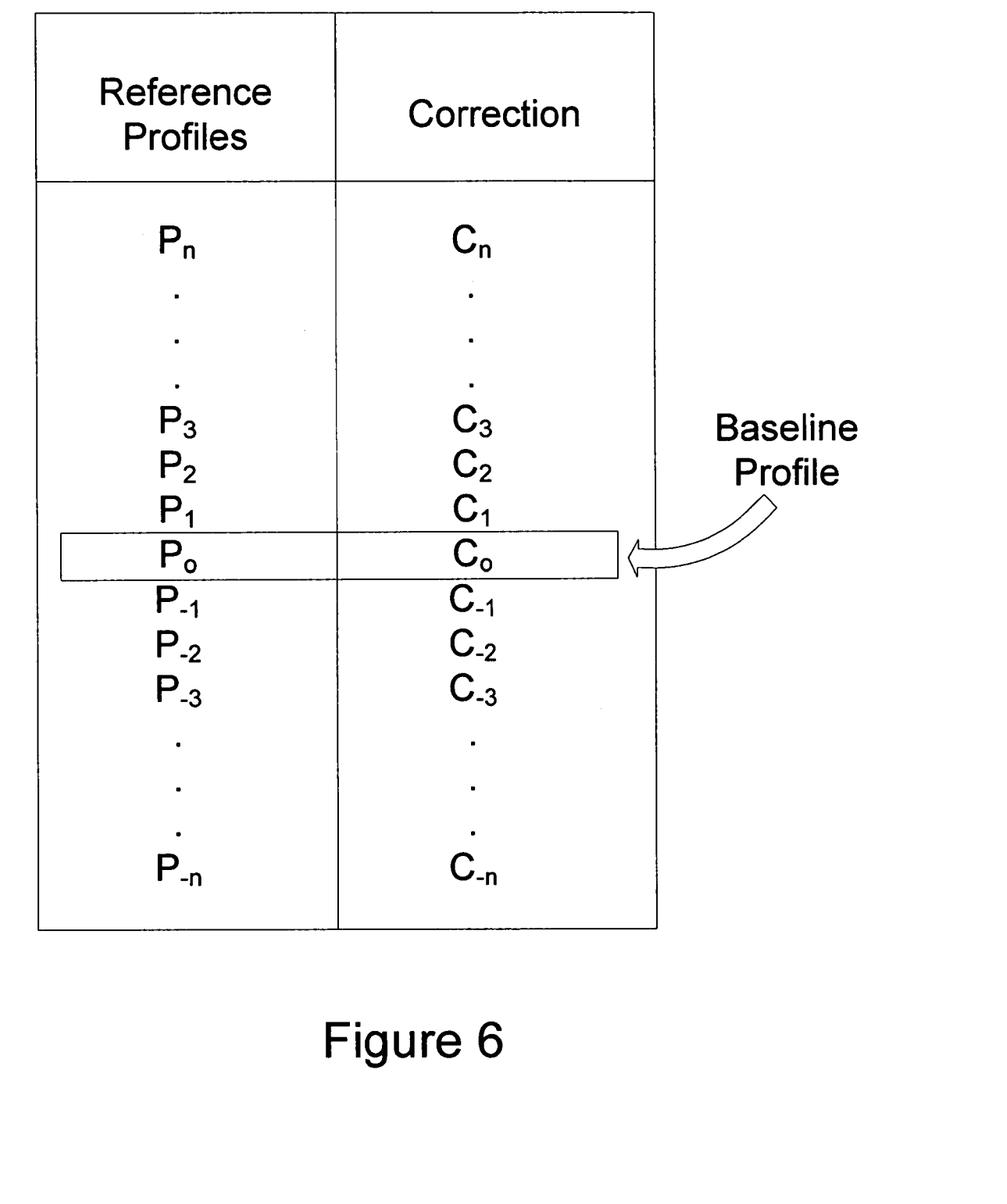
FIG. 6 shows a diagrammatic representation of stored reference profiles (P) and associated correction functions (C) including a stored baseline profile ($P_0$) and associated null correction function ($C_0$).

In particular embodiments utilizing a system including at least a detector and a test sample, focusing can be carried out by matching a dynamic profile, obtained from the test sample using the detector, with a reference profile and adjusting the system based on a correction function associated with the reference profile. A set of reference profiles can be obtained for a test sample each at a different focus position. For example, as shown in FIG. 6, a set of reference profiles can include those obtained at incremental offsets in one direction (i.e. $P_1$ to $P_n$) and incremental offsets in an opposite direction (i.e. $P_{-1}$ to $R_{-n}$), both relative to a configuration that yields a baseline profile, the baseline profile representing a desired focus. A correction function (C) specifying an adjustment of the system capable of bringing a sample into focus is associated with each reference profile. In the case of the baseline profile the correction function is shown as a null function, specifying that adjustment of the system is not necessary. A dynamic profile can be obtained for a test sample and compared to one or more of the reference profiles in a set. A match can be identified between the dynamic profile and one of the reference profiles, for example, $P_3$ shown in FIG. 6. The associated correction, $C_3$ in the exemplified case, can be applied to the system to obtain the desired focus. Upon application of the adjustment specified in $C_3$ a dynamic profile obtained for the sample will be matched to the baseline profile $P_0$, indicating that further adjustment of the system is not required to obtain the desired focus.

As used herein, "focusing" refers to the process of adjusting a detection system to obtain a desired characteristic for a representation of an object being detected. For example, an optical detection system can be adjusted to increase sharpness, contrast or modulation transfer function (MTF) for an image of a test sample being detected. By way of further example, an optical detection system can be adjusted to obtain an image having a desired uniformity, and in particular embodiments the image can have both a desired uniformity and an MTF that is above a defined minimum value. The MTF for an image can vary at different locations of a sample being detected. For example, MTF can be different at two separate locations of a sample to allow the image to have one or more other characteristics that a similar or within a desired range at each of the locations.

As used herein, "imaging system" refers to a device that produces a representation of a sample or portion thereof. An imaging system can include a scanner that produces an image or representation of a sample by collecting optical data as the relative location of the sample and detection device are changed. Imaging scanners may include confocal scanners. Confocal scanners may include a laser directed from a radiation source through an objective lens. The objective lens can focus the laser to a focus area. Radiation can be directed from a focus area of a sample to one or more detectors through an aperture positioned to allow only radiation reflected from the focus area to pass therethrough. It will be understood that an imaging system need not scan an object and can stare at a sample or portion thereof to obtain signals that are used to produce a representation of the object. Examples of detectors that can stare at an object include, for example, charge coupled devices.

As used herein, "detection region" refers to a sample, or portion thereof, from which an image is to be produced. A detection region is typically a monolayer. However, a region detected in a method of the invention can include one, two or three dimensions. If desired, a detection region can be limited to one or two dimensions excluding the second or third dimension of a sample, respectively. A test sample from which an image is to be produced can include an array of probes, collection of particles or molecules, organism, organ, tissue, cell, biological isolate, cell culture or the like. A test sample can further include a substrate, such as a slide, having a sample supported or suspended thereon. An exemplary detection region is a detection line. A detection line can include 2 or more points that are detected. The line can be detected by scanning or by staring.

As used herein, the term "array" refers to a population of different probe molecules that are attached to one or more substrates such that the different probe molecules can be differentiated from each other according to relative location. An array can include different probe molecules that are each located at a different addressable location on a substrate. Alternatively, an array can include separate substrates each bearing a different probe molecule, wherein the different probe molecules can be identified according to the locations of the substrates on a surface to which the substrates are attached or according to the locations of the substrates in a liquid. Exemplary arrays in which separate substrates are located on a surface include, without limitation, those including beads in wells as described, for example, in U.S. Pat. No. 6,355,431 B1, US 2002/0102578 and PCT Publication No. WO 00/63437. Further examples of arrays that can be used in the invention include, without limitation, those described in Butte, *Nature Reviews Drug Discov.* 1:951-60 (2002) or U.S. Pat. Nos. 5,429,807; 5,436,327; 5,561,071; 5,583,211; 5,658,734; 5,837,858; 5,874,219; 5,919,523; 6,136,269; 6,287,768; 6,287,776; 6,288,220; 6,297,006; 6,291,193; 6,346,413; 6,416,949; 6,482,591; 6,514,751 and 6,610,482; and WO 93/17126; WO 95/11995; WO 95/35505; EP 742 287; and EP 799 897.

As used herein, "profile," when used in reference to a sample, refers to a representation of one or more characteristics of the sample, or portion thereof. Exemplary characteristics include, without limitation, optical characteristics such as intensity, resolution, contrast, phase and aberration. A profile may be expressed as a series of values, graph of values, table of values, image, polynomial function, or combination thereof for example. A profile can relate characteristics or parameters of a sample to one or more coordinates located in the sample.

As used herein, "dynamic profile" refers to a profile of a sample obtained at a specific time. A dynamic profile may be obtained by measuring fluorescence, reflectance, scatter, polarization or other property of irradiation derived from a particular detection region.

As used herein, "reference profile" refers to a profile to which another profile, such as a dynamic profile, is compared. Typically a reference profile is obtained at a different point in time compared to a dynamic profile. A reference profile can be stored, for example, in a computer readable memory.

As used herein, "baseline profile" refers to a reference profile for an optical system that is at a desired focus. Accordingly, a baseline profile is a reference profile that is matched to a dynamic profile with no correction, with a best fit compared other reference profiles or with an otherwise desired fit.

As used herein, "stored" refers to holding of information or data in a tangible medium. Exemplary media include, without limitation, a computer readable memory, paper or other material to which information can be written and read.

As used herein, "correction" refers to a function or set of instructions that specifies an adjustment to an optical system that alters a characteristic of an image in a desired or expected way. Exemplary adjustments include those that are mechanical, optical or informatic in nature. Mechanical adjustments include, for example, repositioning of one or more components of an imaging system, such as an objective lens, detector or sample stage. Optical adjustments include, for example, changes in reflection or refraction of light by an optical element, alteration of an electrical charge across a CCD camera or change in the index of refraction of an optical element. Adjustment of the index of refraction can include, for example, providing a lens with a fluid cavity though which light passes, and changing the density of the fluid within the cavity to control the index of refraction of the lens. An informatic adjustment can be made to alter a recorded signal, for example, in a computer readable memory. Such adjustments can result, for example, in repositioning of an optical element of a detection system, changing a characteristic of an optical element of a detection system or other manipulation of the path of radiation emanating from a test sample in an optical system.

In one embodiment, a mechanical correction includes a z-axis translation. The term "z-axis" is intended to be consistent with its use in the art of microscopy such that the z-axis is the same as the focal axis. Accordingly, a z-axis translation results in increasing or decreasing the length of the focal axis. A z-axis translation can be carried out, for example, by moving a sample stage relative to an optical element or by moving an optical element relative to the sample stage. As such, z-axis translation can be carried out by driving an objective lens or sample stage, either of which can be driven by actuating a servo or a motor that is in functional communication with the objective lens and/or the sample stage. Exemplary optical elements include, but are not limited to lenses, prisms or other elements that direct, shape or otherwise manipulate radiation.

As used herein, "sample stage" refers to a solid support or other means for holding a test sample. The sample stage is generally positioned along the radiation path of radiation entering or exiting an objective lens.

As used herein, "pattern-matching" refers to an algorithm for comparing the characteristics of two data sets. Exemplary data that can be compared include, without limitation, images, optical intensities, colors, physical locations or the like. The pattern may include a chart; image, such as a bit-map image; series of values; table of values, or other representation of a profile. According to a typical pattern matching algorithm a function is defined to take arguments of a particular type, form or value. When applying the function to its actual arguments the type, form or value of the actual arguments is matched against the formal arguments in a definition. Pattern-matching analysis may use algorithms such as principal component analysis and filter matching.

As used herein, the term "radiation source" is intended to mean an origin or generator of propagated electromagnetic energy. The term can include any illumination sources including, for example, a light source. A light source useful in the invention can produce electromagnetic radiation in the ultraviolet, visible and/or infrared regions of the spectrum. A radiation source can include, for example, a lamp such as an arc lamp or quartz halogen lamp, or a laser. A radiation source that produces electromagnetic radiation outside of the ultraviolet, visible and/or infrared regions of the spectrum can also be useful in particular embodiments of the invention.

As used herein, the term "laser" is intended to mean a source of radiation produced by light amplification by stimulated emission of radiation. The term can include, for example, an ion laser such as argon ion or krypton ion laser, helium neon laser, helium cadmium laser, dye laser such as a rhodamine 6G laser, YAG laser or diode laser. These and other lasers useful in the apparatus of the invention are known in the art as described, for example, in Shapiro, *Practical Flow Cytometry*, 3rd Ed. Wiley-Liss, New York (1995).

Figure 1:
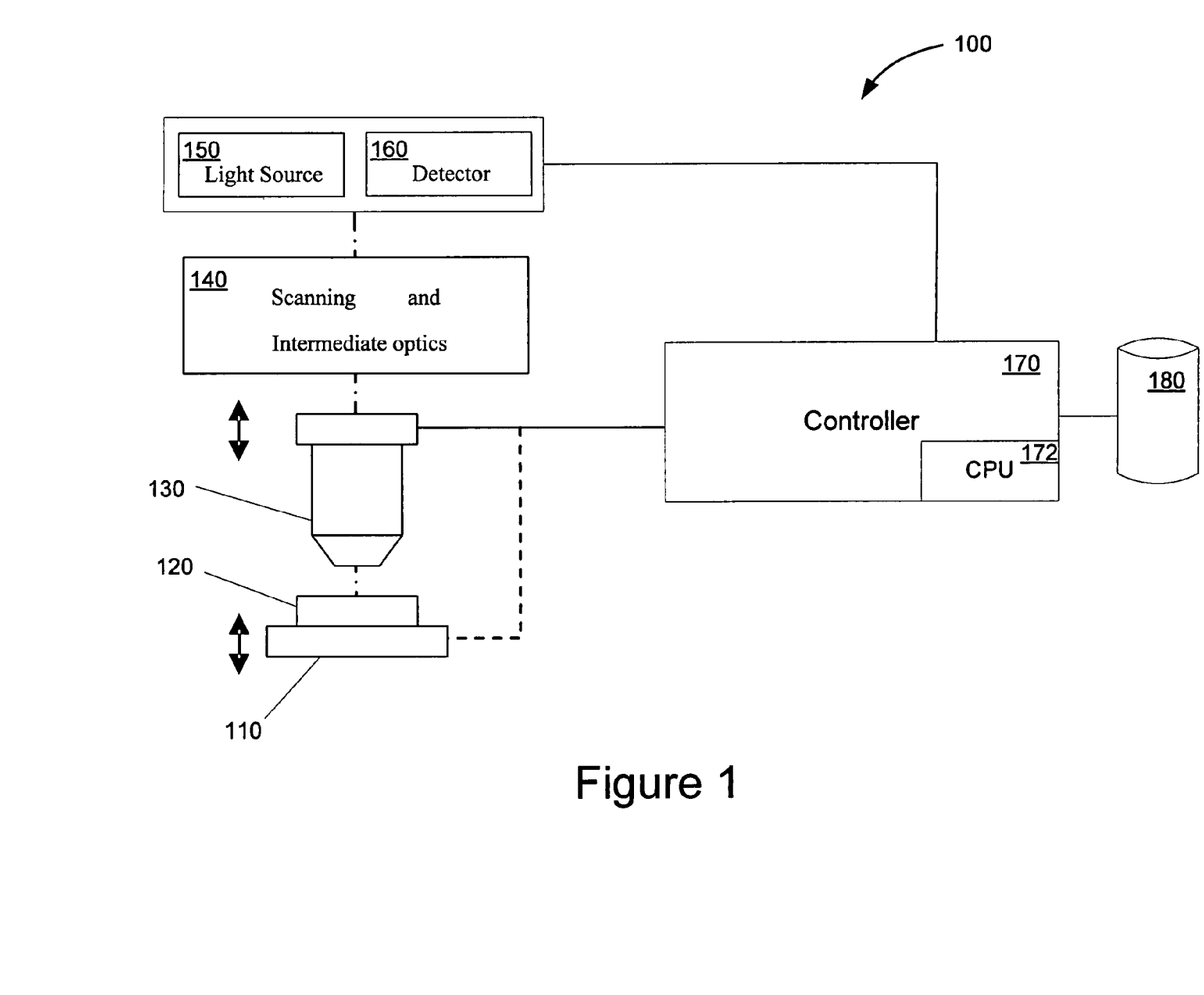
FIG. 1 is a schematic illustration of an embodiment of an imaging system.

Referring to FIG. 1, an embodiment of an image scanning system, such as a confocal microscope, is illustrated. The imaging scanning system 100 may include a device for obtaining or producing an image of a region. In one embodiment, the image scanning system 100 is a confocal scanner.

Confocal scanners typically include a laser directed from a light source through an objective lens. The objective lens focuses the laser to a focus area in or on a test sample. The light emanating from a test sample can be directed to one or more detectors through an aperture positioned to allow only light emanating from the focus area to pass therethrough. Thus, the aperture of the confocal scanner improves image quality by filtering out components of the light that emanate from portions of a sample that are outside of the focus area. For additional details on confocal scanners, reference may be made to U.S. Pat. Nos. 5,847,400 and 5,754,291, each of which is hereby incorporated by reference in its entirety.

An imaging device of the invention is useful for focusing a detector at any of a variety of resolutions. The invention is particularly useful for imaging samples at resolutions capable of differentiating features that are separated on average by a distance of at least about 1 mm, 0.5 mm, 0.01 mm, 1 micron, 0.8 micron, 0.5 micron, 0.3 micron, 0.2 micron, 0.1 micron or less. However, the methods can be used to resolve features that are space on average no more than about 1 cm, 0.5 cm, 1 mm, 0.5 mm, 0.01 mm, 1 micron, 0.8 micron, 0.5 micron, 0.3 micron, 0.2 micron, 0.1 micron or less. Furthermore, the invention can be used to resolve features within these ranges including distances not explicitly listed or to resolve features that are spaced at distances outside of the above ranges.

The image scanning system 100 may be used for a variety of applications, such as imaging of biological materials, for example. The image scanning system 100 includes a sample stage 110 for supporting a test sample 120 thereon. The sample stage 110 may be a support surface or other means for supporting the test sample 120. The sample stage 110 is generally positioned along the radiation path of the radiation exiting an objective lens 130. The sample stage 110 may be formed of a variety of materials, such as metals, and should be sufficiently stable to support the test sample 120 in a stable manner. Other materials that can be used for a sample stage include, without limitation, those set forth above in regard to substrates for arrays.

Figure 2:
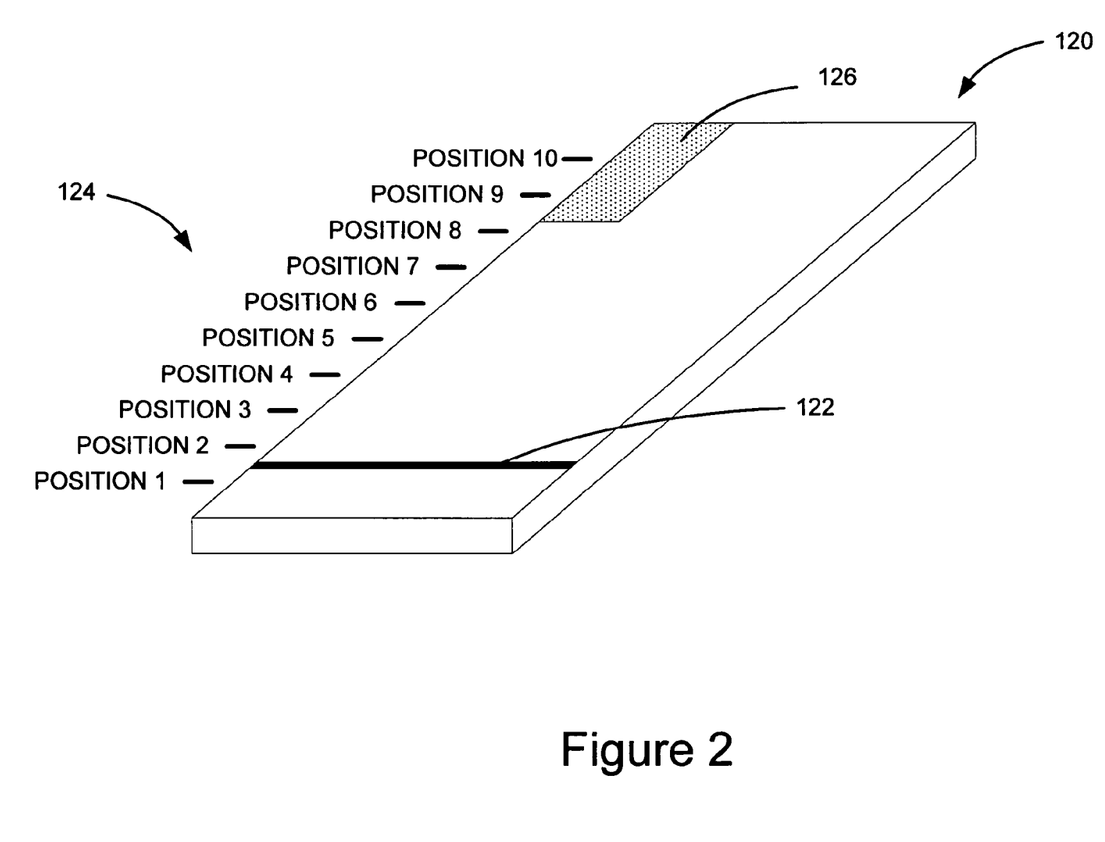
FIG. 2 illustrates an embodiment of a test sample slide.

A test sample 120 may be a slide including a substrate upon which a biological sample or other sample is supported or suspended. One embodiment of the test sample 120 is illustrated in FIG. 2 and described below.

Accordingly, the invention is useful for detecting target molecules that interact with probes in or on an array. Exemplary probes and target molecules include, but are not limited to polynucleotides; polypeptides; biologically active molecules such as biopolymers; or other molecules. A polynucleotide can be DNA, such as genomic DNA (gDNA) or copy DNA (cDNA); RNA such as messenger RNA (mRNA), transfer RNA (tRNA), ribosomal RNA (rRNA), antisense RNA (aRNA) or RNA inhibitor (RNAi); or a hybrid, where the polynucleotide contains any combination of deoxyribo- and ribo-nucleotides, and any combination of bases, including uracil, adenine, thymine, cytosine, guanine, inosine, xanthanine, hypoxathanine, isocytosine, isoguanine, or the like. Particular embodiments utilize isocytosine and isoguanine as is generally described in U.S. Pat. No. 5,681,702. A polypeptide useful in the methods and compositions described herein can have naturally occurring amino acids and peptide bonds, or synthetic peptidomimetic structures. The side chains may be in either the (R) or the (S) configuration. In a particular embodiment, the amino acids are in the (S) or L-configuration. If non-naturally occurring side chains are used, non-amino acid substituents may be used. Exemplary polypeptides that can be made and used include, without limitation, an antigen, immunoglobulin, antibody, enzyme, ligand binding receptor, T-cell receptor, kinase, phosphatase, lectin, G-protein coupled receptor, or functional fragments thereof. The functional fragments having, for example, binding specificity for a ligand of the full length polypeptide.

In particular embodiments, the presence of one or more target molecules in a sample can be detected based on the presence of the probe, target or both in a bound complex. For example, a pre-labeled DNA fragment having a sequence of interest can be identified based on presence of the label at a particular array location where a complementary nucleic acid probe resides. Alternatively, probes or targets in a complex can be modified, thereby allowing detection. For example, in embodiments utilizing nucleic acid targets and complementary nucleic acid probes methods such as allele-specific primer extension (ASPE), single base extension (SBE), oligonucleotide ligation amplification (OLA), rolling circle amplification (RCA), extension ligation (GoldenGate™), invader technology, probe cleavage or pyrosequencing can be used to modify the probe, target or both. Such methods can be carried out, for example, as described in U.S. Pat. No. 6,355,431 B1 or U.S. Ser. No. 10/177,727.

A detection system of the invention will typically have sufficient resolution to differentiate features of an array. Features of an array can include discrete sites where a particular type of probe resides. In particular embodiments, the features are particles having attached probes. Exemplary particles include microspheres, beads or other shapes such as cylinders, disks, plates, chips, slivers or irregular shapes. Particle sizes can range, for example, from nanometers such as about 100 nm beads, to millimeters, such as about 1 mm beads, with particles of intermediate size such as at most about 0.2 micron, 0.5 micron, 5 micron or 200 microns being useful. Discrete sites can be wells, channels, locations having an adhesive surface or locations having chemical functionalities useful for attaching particles.

Bead-based arrays that can be used in the invention include, without limitation, those in which beads are associated with a solid support such as those described in U.S. Pat. No. 6,355,431 B1, US 2002/0102578 and PCT Publication No. WO 00/63437. Beads can be located at discrete locations, such as wells, on a solid-phase support, whereby each location accommodates a single bead. Alternatively, discrete locations where beads reside can each include a plurality of beads as described, for example, in US Pat. App. Nos. US 2004/0263923, US 2004/0233485, US 2004/0132205, or US 2004/0125424.

Beads or other particles can be loaded onto array supports using methods known in the art such as those described, for example, in U.S. Pat. No. 6,355,431. In some embodiments, for example when chemical attachment is done, particles can be attached to a support in a non-random or ordered process. For example, using photoactivatible attachment linkers or photoactivatible adhesives or masks, selected sites on an array support can be sequentially activated for attachment, such that defined populations of particles are laid down at defined positions when exposed to the activated array substrate. Alternatively, particles can be randomly deposited on a substrate. In embodiments where the placement of probes is random, a coding or decoding system can be used to localize and/or identify the probes at each location in the array. This can be done in any of a variety of ways, for example, as described in U.S. Pat. No. 6,355,431 or WO 03/002979. A further encoding system that is useful in the invention is the use of diffraction gratings as described, for example, in U.S. Pat. App. Nos. US 2004/0263923, US 2004/0233485, US 2004/0132205, or US 2004/0125424.

Arrays that are useful in the invention can be non-bead-based. A particularly useful array is an Affymetrix® GeneChip® array. GeneChip® arrays can be synthesized in accordance with techniques sometimes referred to as VLSIPS™ (Very Large Scale Immobilized Polymer Synthesis) technologies. A spotted array can also be used in a method of the invention. An exemplary spotted array is a CodeLink™ Array available from Amersham Biosciences. An array that is useful in the invention can also be manufactured using inkjet printing methods such as SurePrint™ Technology available from Agilent Technologies.

Features of bead-based or non-bead-based arrays can be present at any of a variety of densities. Very high density arrays are useful in the invention including, for example, those having from about 10,000,000 features/cm$^2$ to about 2,000,000,000 features/cm$^2$ or from about 100,000,000 features/cm$^2$ to about 1,000,000,000 features/cm$^2$. High density arrays can also be used including, for example, those in the range from about 100,000 features/cm$^2$ to about 10,000,000 features/cm$^2$ or about 1,000,000 features/cm$^2$ to about 5,000,000 features/cm$^2$. Moderate density arrays useful in the invention can range from about 10,000 features/cm$^2$ to about 100,000 features/cm$^2$, or from about 20,000 features/cm$^2$ to about 50,000 features/cm$^2$. Low density arrays are generally less than 10,000 features/cm$^2$ with from about 1,000 features/cm$^2$ to about 5,000 features/cm$^2$ being useful in particular embodiments. Very low density arrays having less than 1,000 features/cm$^2$, from about 10 features/cm$^2$ to about 1000 features/cm$^2$, or from about 100 features/cm$^2$ to about 500 features/cm² are also useful in some applications. An imaging system useful in the invention can have resolution capable of differentiating features of at least the above-listed densities.

An array of arrays or a composite array, having a plurality of individual arrays that is configured to allow processing of multiple samples, can also be detected in the invention. Such arrays allow multiplex detection. Thus the surface of a solid-phase support can include a plurality of individual arrays that are physically separated from each other. For example, physical separation can be due to the presence of assay wells, such as in a microtiter plate. Other barriers that can be used to physically separate array locations include, for example, gaskets, raised barriers, channels, hydrophobic regions that will deter flow of aqueous solvents or hydrophilic regions that will deter flow of apolar or hydrophobic solvents. Exemplary composite arrays that can be used in the invention, for example, in multiplex detection formats are described in U.S. Pat. No. 6,429,027 and US 2002/0102578.

A solid-phase support used in an array of the invention can be made from any material that can be modified to contain discrete individual sites or to attach a desired probe. In embodiments where arrays of particles are used, a material that is capable of attaching or associating with one or more type of particles can be used. Useful supports include, but are not limited to, glass; modified glass; functionalized glass; plastics such as acrylics, polystyrene and copolymers of styrene and other materials, polypropylene, polyethylene, polybutylene, polyurethanes, Teflon, or the like; polysaccharides; nylon; nitrocellulose; resins; silica; silica-based materials such as silicon or modified silicon; carbon; metal; inorganic glass; optical fiber bundles, or any of a variety of other polymers. Useful supports include those that allow optical detection, for example, by being translucent to energy of a desired detection wavelength and/or do not themselves appreciably fluoresce at particular detection wavelengths. In a particular embodiment, an array support can be an optical fiber bundle or array, as is generally described in U.S. Ser. No. 08/944,850, U.S. Pat. No. 6,200,737; WO 98/40726, and WO 98/50782. Similar materials can be included in a sample stage or sample used in the invention.

Referring again to FIG. 1, the objective lens 130 can be adapted to focus radiation onto a point or region of the test sample 120. In confocal imaging systems, the location of the focus area is typically a function of the characteristics of the objective lens. Thus, the distance between the objective lens 130 and the area of the test sample 120 desired to be imaged is at least in part a function of certain characteristics of the objective lens 130. In this regard, the relative position of the sample stage 110 and the objective lens 130 along a z axis or z direction (vertical direction in FIG. 1) can be adjusted through movement of at least one of the sample stage 110 and the objective lens 130, as indicated by the double arrows in FIG. 1. This vertical movement may be accomplished through a servo actuator, for example.

The image scanning system 100 can also include a radiation source 150, scanning and intermediate optics 140 and a detector 170. The radiation source 150 may be adapted to produce radiation for illumination of the test sample 120. In confocal scanners, the radiation source 150 may be a laser such as an argon ion laser or an argon/krypton mixed gas laser. Of course, other embodiments may be implemented using other types of lasers or light sources.

The radiation from the radiation source 150 can be directed toward the objective lens 130 and the test sample 120 through intermediate optics 140. The intermediate optics 140 may include one or more lenses, mirrors or other optical elements adapted to manipulate or direct the radiation from the radiation source. In confocal scanners, the scanning and intermediate optics 140 may include movable reflective surfaces, such as mirrors or prisms, which allow radiation to traverse through the objective lens and contact a region of the test sample. In this regard, the light may traverse in either one, two or three dimensions.

The radiation striking the test sample 120 can have an interaction that causes radiation to emanate from the sample. For example, the radiation can be reflected or scattered by the sample. In particular embodiments, radiation can be absorbed by the sample. The sample can, in turn, emit fluorescence or luminescence. A sample need not be irradiated in order to emanate radiation. For example, a chemiluminescent material can produce light in response to a chemical reaction and the resulting light emanating from the material can be detected using methods or devices set forth herein.

Radiation emanating from a sample can pass back through the objective lens 130 and the intermediate optics for detection by a detector 160. The detector 160 may be a photodetector adapted to detect or measure light emanating from the sample. Signals produced by a photodetector can be used for producing an image of the test sample. Signal processing can be carried out using hardware and methods known in the art. In various embodiments, the detector 160 may include a photomultiplier, a charge coupled device (CCD), a complementary metal oxide semiconductor (CMOS), a photomultiplier tube (PMT), an avalanche photodiode detector, a photodiode or a combination thereof. In one embodiment, the detector 160 includes a single element detector, while in other embodiments, a detector array may be implemented.

The image scanning system 100 can also include a controller 170 for, among other functions, facilitating the focusing of the image scanning system 100. The controller 170 may be adapted to provide instructions to the radiation source 150 or other optical components such as scanning optics or intermediate optics 140 to control the imaging or scanning of the system 100. Further, the controller 170 may receive signals from the detector 160 including detected or measured data from the test sample 120.

As noted above, the controller 170 can be adapted to facilitate the focusing of the image scanning system 100. In this regard, focusing can include a process of adjusting optical equipment to obtain a sharper image, for example. Focusing may include an optical correction through manipulation of the path of radiation being directed to or emanating from a region of the test sample 120 to be scanned. The manipulation may include changes in reflection or refraction of radiation or distances between components along the radiation path.

In the embodiment illustrated in FIG. 1, the controller 170 of the image scanning system 100 is adapted to transmit signals to the objective lens 130, the sample stage 110 or both, thereby causing a relative z-axis translation between the objective lens 130 and the sample stage 110. In this regard, the controller 170 may include a processor 172 to receive signals from the detector 160, determine a desired correction and send signals that specify adjustment of one or more components of the imaging system. In the embodiment illustrated in FIG. 1, the signals may actuate one or more servos to cause the z-axis translation.

In other embodiments, an adjustment specified by processor 172 can include an adjustment of an index of refraction of one or more optical elements in, for example, the scanning or intermediate optics 140. The optical elements in the scanning and intermediate optics 140 may include lenses, prisms or other elements that shape, pass, direct or otherwise manipulate radiation. Adjustment of the index of refraction may include a mechanical or electrical alteration of the optical element for causing a change in the element's ability to bend light. For example, a lens may be provided with a fluid cavity though which light passes, and the density of the fluid within the cavity may be adjusted to control the index of refraction of the lens.

The image scanning system 100 can also include a memory device 180 for storing data such as a computer readable memory. Exemplary forms of computer readable memory include, but are not limited to, a database, hard disk, floppy disc, compact disc, magneto-optical disc, Random Access Memory, Read Only Memory or Flash Memory. The memory or computer readable medium used in the invention can be contained within a single computer or distributed in a network. A network can be any of a number of conventional network systems known in the art such as a local area network (LAN) or a wide area network (WAN). Client-server environments, database servers and networks that can be used in the invention are well known in the art. For example, the database server can run on an operating system such as UNIX®, running a relational database management system, a World Wide Web application or a World Wide Web server. Other types of memories and computer readable media are also contemplated to function within the scope of the invention.

Information stored in accordance with the invention can be in any of a variety of forms known in the art including, for example, a text file, .xml file, jpg file, TIFF file, or BMP file. Software to implement a method of the invention can be written in any well known computer language, such as Java, C, C++, Visual Basic, FORTRAN or COBOL and compiled using any well-known compatible compiler. The software of the invention normally runs from instructions stored in a memory on a host computer system. A database or data structure of the invention can be represented in a markup language format including, for example, standard generalized markup language (SGML), hypertext markup language (HTML) or extensible markup language (XML).

Referring now to FIG. 2, an exemplary test sample 120 is illustrated. The test sample 120 includes a slide that has a substantially rectangular configuration and a region desired to be imaged. In various embodiments and various applications, the slide may include a substrate with a sample supported thereupon or suspended therein. Those skilled in the art will understand that the slide may be formed in various shapes and sizes and may be configured to support a sample in various manners.

During the imaging process, the entire slide may be imaged. Alternatively or additionally, the slide may be divided into detection regions, and the imaging may be performed region by region. For example, a BeadChip array (Illumina, Inc., San Diego) having multiple sections, each measuring about 1.8 cm×16 cm, can be scanned section by section such that a collection of signals capable for producing a complete image of a first section are collected prior to initiating imaging of a second section. Alternatively, the entire slide can be scanned such that signals are collected from multiple sections before a collection of signals capable of producing an image of any one of the sections is fully acquired. In various embodiments, the detection region may include one or more scan lines 122. Each scan line may correspond to the area of a sample that is detected when excitation radiation from a radiation source, such as a laser, is directed across one dimension of the test sample 120. The pixel resolution for each scan line can be, for example, at least about 0.2 microns. As pixel resolution decreases scan time can be increased. Accordingly, scan lines useful in the invention can be, for example, at least about 0.4 microns, 0.5 microns, 0.6 microns, 0.8 microns, 0.9 microns, 1.0 microns, 1.5 microns, 20 microns or more.

In other embodiments, the detection region may include a two-dimensional scan area 126. Accordingly, a two-dimensional scan area corresponds to the area of a sample that is detected when excitation radiation is directed across two dimensions of the test sample 120. For example, a collection of contiguous scan lines can be obtained and combined to produce a two-dimensional scan area. In FIG. 2, the two-dimensional scan area 126 has a substantially rectangular configuration. For such two-dimensional scan areas, a CCD detector may be used to detect or measure radiation emanating from the scan area.

As illustrated in FIG. 2, the slide of the test sample 120 may be configured as a rectangle with a short dimension (width) and a long dimension (length). The width can be referred to as the scan direction since the radiation may traverse a scan line along that direction, as indicated by the scan line 122. However, it will be understood that scanning can occur in any desired direction relative to the dimensions of a test sample or substrate upon which the test sample resides. In particular embodiments, a microscope slide or a substrate having a surface with substantially the same dimensions as the face of a standard microscope slide can be used in the invention. Accordingly, a substrate can have a surface area of about 7.5 cm by about 2.5 cm (about 3 inches by about 1 inch). A substrate can further have the thickness of a microscope slide which is about 1 mm (about 0.04 inch). An advantage of using substrates having standard microscope slide dimensions is that existing instrumentation useful for detecting or manipulating samples are configured to accept substrates of this size.

Figure 3:
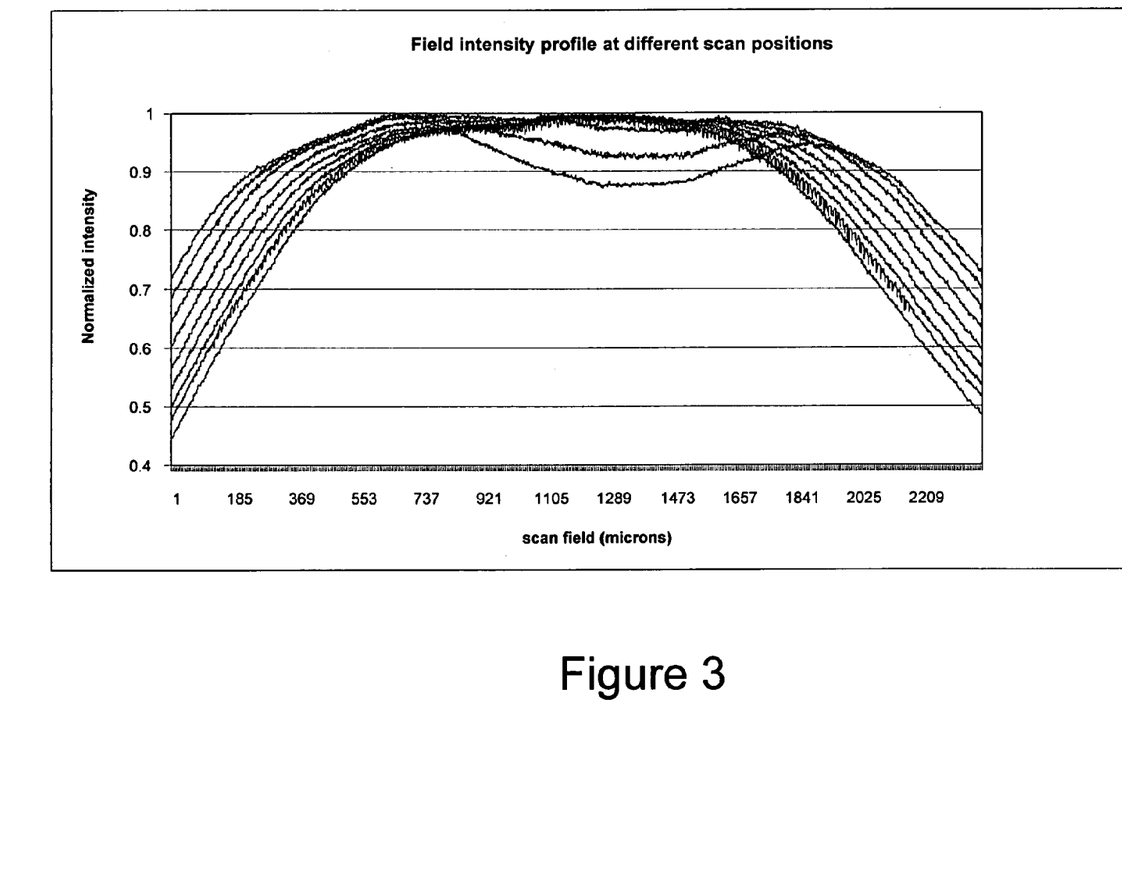
FIG. 3 illustrates exemplary intensity profiles at various positions on the test sample slide of FIG. 2.

With some slides, the length may be large enough such that a tilt, warp or bend in the slide may require adjustment in the relative distance between a sample stage holding the slide and one or more optical components that direct radiation emanating from the slide. Such adjustment can facilitate accurate focusing along the length of the slide. As indicated in FIG. 3, scans at various positions on the slide, as indicated by reference numeral 124 in FIG. 2, may result in non-uniform measurements. FIG. 3 illustrates profiles for scans at each of the positions 124. A profile may include optical characteristics relating to the scanning of an image. The optical characteristics may include intensity, resolution, contrast, phase or aberration. In the profiles illustrated in FIG. 3, the optical characteristic is normalized intensity, wherein the maximum intensity is normalized to 1.0. While measurements at certain positions may be properly focused, those at other positions may be out of focus due to warping, tilting or bending of the slide. Exemplary methods of facilitating the focusing of imaging scanner to solve this and other problems are described below with reference to FIGS. 4 and 5.

In exemplary embodiments, and as shown in FIG. 6, a library of reference profiles (P in FIG. 6) may be stored. Each reference profile corresponds to an associated correction (C in FIG. 6). As an example, a reference profile may correspond to an image scanned in an out-of-focus configuration, and the associated correction indicates the correction required to bring the image into focus. Thus, when a dynamic profile is obtained for a scan line, for example, the profile may be compared to one or more reference profiles in the library. Using pattern-matching techniques, for example, individual reference profiles can be compared to the dynamic profile obtained for the test sample. A correction associated with each reference profile indicates any adjustment(s) required to bring the image into focus. Ultimately, the dynamic profile when matched to the baseline profile ($P_0$) indicates that a desired focus has been obtained.

Thus, in one exemplary embodiment, a dynamic profile is obtained for at least a portion of a current detection region, such as a scan line. The dynamic profile can be compared to one or more reference profiles selected from a set of stored reference profiles and a reference profile having a desired fit to the dynamic profile can be selected. Each of the stored reference profiles can be associated with a correction as described previously herein, for example, in reference to FIG. 6. The correction associated with the selected profile can then be applied to the current detection region of the test sample. The process can be repeated until the dynamic profile matches the baseline profile at which no further correction is required. These steps can be repeated for additional detection regions of the test sample.

Figure 4:
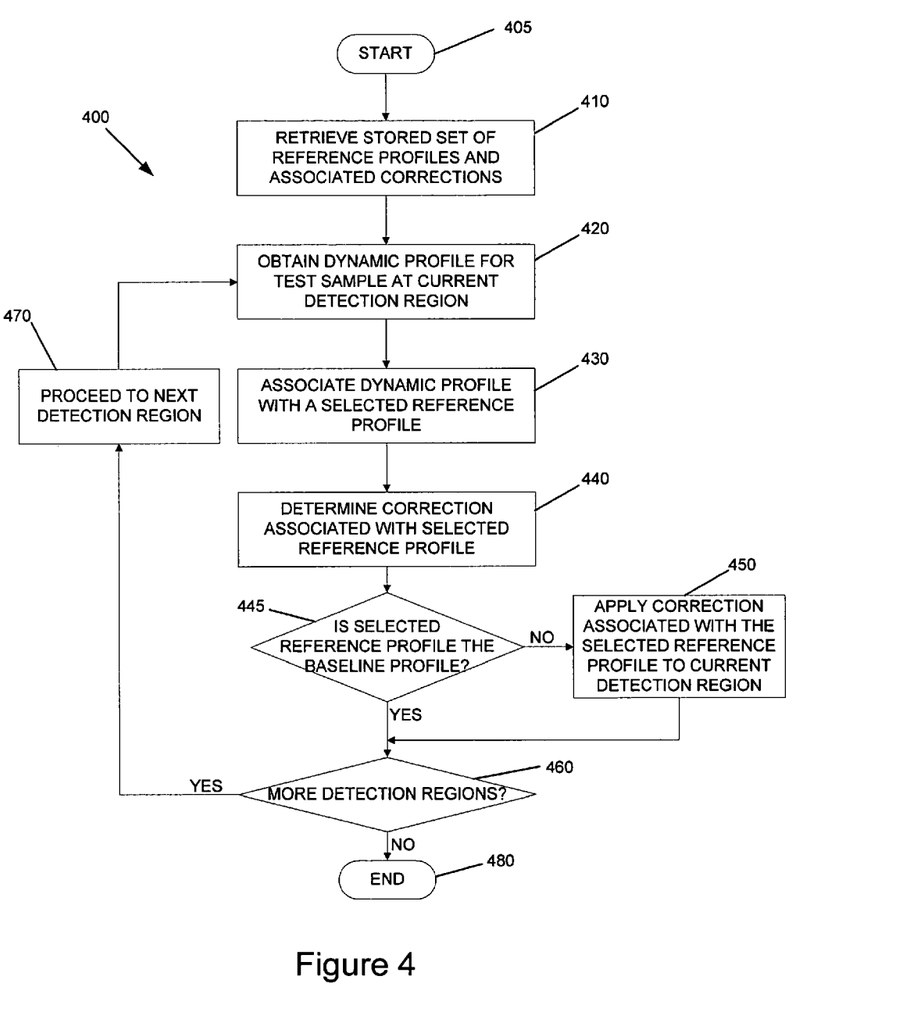
FIG. 4 is a flow chart illustrating an embodiment of a method for facilitating the focusing of an imaging system.

Referring now to FIG. 4, an exemplary embodiment of a method of facilitating the focusing of an imaging system is illustrated. The method 400 includes retrieving a stored set or library of reference profiles (block 410). The reference profiles may be stored in a memory device such as a database or other form set forth herein previously and can be stored in any of a variety of formats such as those set forth previously herein. Each reference profile can be associated with an actual or estimated correction based on, for example, a separate calibration process.

At block 420, a dynamic profile is obtained for the test sample at the current detection region. In the case of scan lines, each detection region corresponds to one or more scan lines. For example, a single detection region may include twenty scan lines. The profile obtained for a single scan line may be used to focus the scanning system for the twenty scan lines in the detection region.

In certain embodiments, a profile may include values for one or more parameters at each of two or more points. In other embodiments, the profile may include at least two parameters at one or more points. The parameters may include intensity, resolution, contrast, phase, aberration or the like.

In obtaining the dynamic profile, radiation from a radiation source may be directed and scanned along the current detection region. The dynamic profile may be obtained by measuring the fluorescence, the reflectance or other form of radiation emanating from the sample at the current detection region.

At block 430, the obtained dynamic profile is associated with a reference profile from the stored set or library of reference profiles. In one embodiment, the association of the dynamic profile to a stored baseline profile is achieved by performing a pattern-matching analysis. The pattern-matching analysis can be used to select one of the stored baseline profiles as the best match, for example. Pattern-matching analyses may include any of various algorithms for comparing, approximating or matching a pattern. The pattern may include a chart, a series or table of values, or other representation. Pattern-matching analyses may include the use of algorithms such as principal component analysis and filter matching, among others.

The correction of the selected reference profile can then be determined (block 440). The determination of the correction may merely include a look-up of a value, function, instruction, or other type of correction associated with the selected reference profile. In some embodiments, the reference profile may provide a range of values, and the determination of the correction may require processing of the values, such as interpolation or extrapolation, for example.

Next, at block 445 a determination can be made as to whether or not correction is required. If the reference file that best matches the dynamic profile is the baseline profile, then no correction is required and the process can move forward to block 460. However, if correction is required the process can loop back to block 450, where the correction is applied to the imaging system (block 450). As noted above, the correction may include adjustment of a relative positioning of two or more components, such as the objective lens 130 and the sample stage 110 of FIG. 1. In this regard, the application of the correction may including driving one or both of the components along the z axis by actuating a servo or a motor to cause translation of the objective lens 130 and/or the sample stage 110. The process can then return to block 430 and can be repeated until the dynamic profile matches the baseline profile.

At block 460, a determination may be made as to whether additional detection regions remain. If other detection regions remain, the method can proceed to block 470 where the imaging system advances to the next detection region. Next, a dynamic profile is obtained (block 420) for the next detection region. If, on the other hand, no addition detection regions remain at block 460, the method can terminate at block 480.

Figure 5:
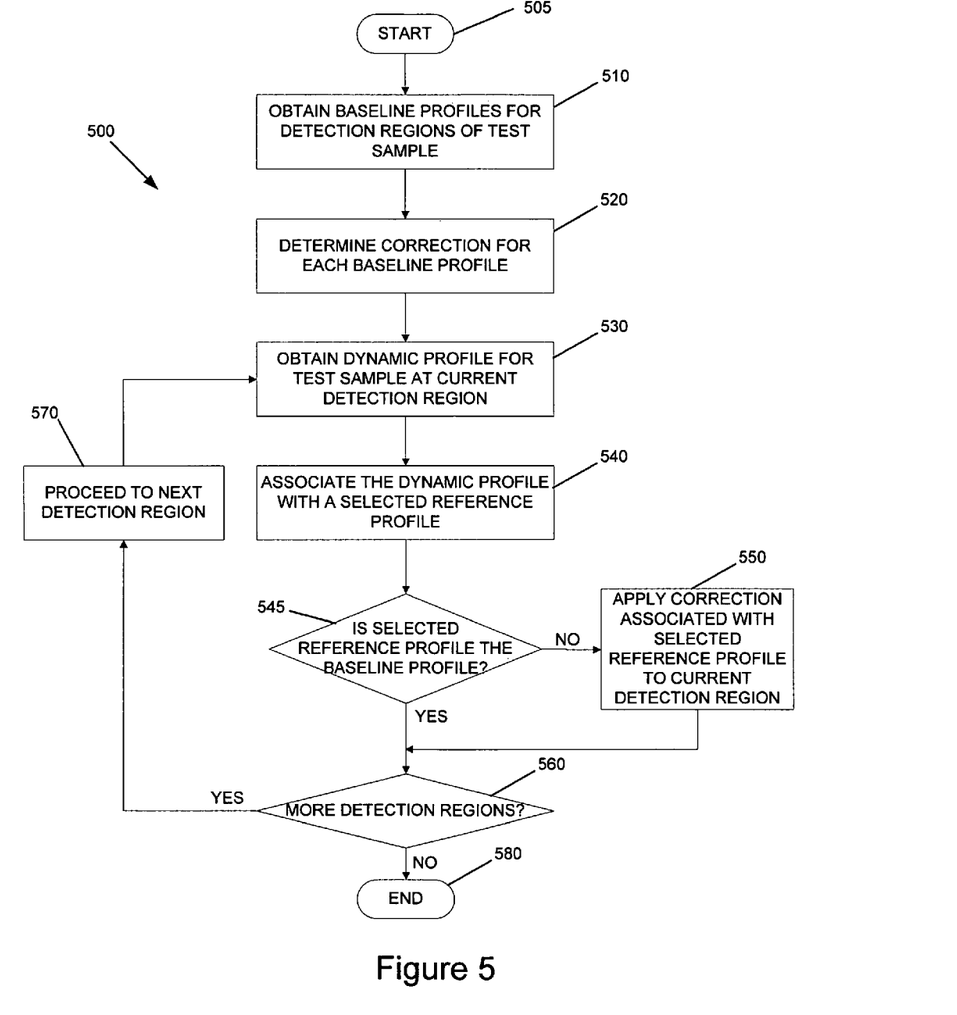
FIG. 5 is a flow chart illustrating another embodiment of a method for facilitating the focusing of an imaging system.

In another exemplary method, illustrated in FIG. 5, reference profiles and the associated correction are generated from the test sample itself. Thus, the method 500 begins by obtaining a set of reference profiles from one or more detection regions. In this regard, one or more specific regions of the test sample or the sample stage may be allocated for precise calibration of the imaging system, if desired. A set of reference profiles may be extracted from this region by varying the z-axis position of the objective lens.

At block 520, a correction may be determined for each reference profile including a baseline profile which can be assigned a null correction. For example, the correction assigned to a reference profile can specify relative displacement of the objective lens and the null correction can specify that no change is required for the relative placement of the objective lens.

At block 530, a profile can be obtained for the test sample at the current detection region. As noted above, in the case of scan lines, each detection region can correspond to one or more scan lines. For example, a single detection region may include twenty scan lines. The profile obtained for a single scan line may be used to focus the scanning system for the twenty scan lines in the detection region.

At block 540, the obtained dynamic profile is associated with a reference profile from the set of reference profiles. A pattern-matching analysis may be used to select one of the baseline profiles as the best match, for example, as described previously herein.

Next, at block 545 a determination can be made as to whether or not correction is required. If the reference file that best matches the dynamic profile is the baseline profile, then no correction is required and the process can move forward to block 560. However, if correction is required the process can loop back to block 550. A correction can then be applied to the imaging system (block 550) by, for example, adjusting the relative positioning of the objective lens 130 and the sample stage 110 of FIG. 1 or using other adjustments set forth herein. The process can then return to block 540 and can be repeated until the dynamic profile matches the baseline profile.

At block 560, a determination may be made as to whether additional detection regions remain. If other detection regions remain, the method can proceed to block 540 where the imaging system advances to the next detection region. If, on the other hand, no addition detection regions remain at block 560, the method can terminate at block 580.

Throughout this application various publications, patents and patent applications have been referenced. The disclosure of these publications in their entireties is hereby incorporated by reference in this application in order to more fully describe the state of the art to which this invention pertains.

The term "comprising" in the claims is intended herein to be open-ended, including not only the recited elements, but further encompassing any additional elements.

The foregoing description of embodiments of the invention have been presented for purposes of illustration and description. It is not intended to be exhaustive or to limit the invention to the precise form disclosed, and modifications and variation are possible in light of the above teachings or may be acquired from practice of the invention. The embodiment was chosen and described in order to explain the principles of the invention and its practical application to enable one skilled in the art to utilize the invention in various embodiments and with various modification as are suited to the particular use contemplated. It is intended that the scope of the invention be defined by the claims appended hereto and their equivalents.

The invention claimed is:

1. A method, comprising:
   providing a library of reference profiles, wherein each reference profile includes values for at least one parameter for at least two points of a scanline;
   directing excitation radiation from an optical scanning system across one dimension of a two-dimensional scan area of a test sample;
   obtaining a dynamic profile including at least two points of a scanline of the test sample by detecting radiation emanating from the one dimension of the two-dimensional scan area of the test sample using the optical scanning system;
   comparing the obtained dynamic profile to reference profiles in the library;
   identifying a best fit profile for the obtained dynamic profile from the library of reference profiles; and
   making a correction to the optical scanning system based on the identified best fit profile.

2. The method of claim 1, wherein each reference profile includes values for at least one parameter at two or more points along the one dimension of the two-dimensional scan area.

3. The method of claim 1, wherein the at least one parameter includes a z-axis variation for the at least two points in the scanline.

4. The method of claim 1, wherein the at least one parameter includes at least one of intensity, resolution, contrast, phase, and aberration.

5. The method of claim 1, wherein the reference profiles include spatial variation of at least one of intensity, resolution, contrast, phase, and aberration.

6. The method of claim 1, wherein the obtained dynamic profile and the reference profiles include values for at least two parameters at one or more points.

7. The method of claim 6, wherein the at least two parameters include at least two of intensity, resolution, contrast, phase and aberration.

8. The method of claim 1, wherein obtaining the dynamic profile includes detection of fluorescence or luminescence.

9. The method of claim 1, wherein the obtained dynamic profile includes values for at least one optical property at two or more points along the one dimension of the two-dimensional scan area.

10. The method of claim 1, wherein comparing the obtained dynamic profile to the reference profiles in the library includes pattern matching.

11. The method of claim 1, wherein the correction includes a mechanical adjustment of a z-axis location of the test sample relative to the optical scanning system.

12. The method of claim 11, wherein the mechanical adjustment is carried out by a servo actuator.

13. The method of claim 1, wherein the correction includes an adjustment of an index of refraction of one or more optical elements of the optical scanning system.

14. The method of claim 1, wherein the correction comprises an optical adjustment of the optical scanning system.

15. The method of claim 1, wherein the at least two points of the scanline of the test sample are on a surface of a substrate.

16. The method of claim 15, wherein the substrate includes an array of molecular probes.

17. The method of claim 1, comprising detecting the radiation emanating from the one dimension of the two-dimensional scan area of the test sample using a photodetector.

18. The method of claim 17, wherein the photodetector includes at least one of a photomultiplier, a charge coupled device (CCD), a complementary metal oxide semiconductor (CMOS), a photomultiplier tube (PMT), an avalanche photodiode detector and a photodiode.

19. The method of claim 18, wherein the photodetector is a single element detector.

20. The method of claim 18, wherein the photodetector includes a detector array.

* * * * *